United States Patent
McCracken (10) Patent No.: US 7,058,528 B2
(45) Date of Patent: Jun. 6, 2006

(54) AUTOMATED OPTIMIZATION OF ASYMMETRIC WAVEFORM GENERATOR LC TUNING ELECTRONICS

(75) Inventor: Iain McCracken, Kanata (CA)

(73) Assignee: Ionalytics Corporation, Ottawa (CA)

(*) Notice: Subject to any disclaimer, the term of this patent is extended or adjusted under 35 U.S.C. 154(b) by 86 days.

(21) Appl. No.: 10/854,137

(22) Filed: May 27, 2004

(65) Prior Publication Data

US 2005/0012037 A1    Jan. 20, 2005

Related U.S. Application Data

(60) Provisional application No. 60/486,284, filed on Jul. 11, 2003.

(51) Int. Cl.
*G06F 19/00* (2006.01)
(52) U.S. Cl. .................. 702/66; 702/106; 702/124; 702/189; 327/77; 327/94; 327/95; 331/1 R; 331/2; 331/14; 332/120; 332/125; 382/208
(58) Field of Classification Search .............. 702/66, 702/106, 189, 124, FOR. 170; 327/77, 94, 327/95; 331/1 R, 2, 14; 332/120, 125; 382/208
See application file for complete search history.

(56) References Cited

U.S. PATENT DOCUMENTS

| | | | | |
|---|---|---|---|---|
| 3,940,752 A | * | 2/1976 | Bair | 340/870.11 |
| 5,365,546 A | * | 11/1994 | Koenck et al. | 375/223 |
| 5,420,514 A | * | 5/1995 | Wardle et al. | 324/615 |
| 5,684,850 A | * | 11/1997 | Warburton et al. | 378/53 |
| 5,801,379 A | | 9/1998 | Kouznetsov | |
| 5,847,612 A | * | 12/1998 | Birleson | 331/2 |
| 6,014,064 A | * | 1/2000 | Boles et al. | 331/108 C |
| 6,504,149 B1 | * | 1/2003 | Guevremont et al. | 250/286 |

(Continued)

FOREIGN PATENT DOCUMENTS

EP    0 701 138 A2    3/1996

(Continued)

OTHER PUBLICATIONS

Ben-Hail, 'Autonomous Induction Generator With Single Phase Rotor', Jan. 2000, IEEE Publication, vol. 147, No. 1, pp. 55-60.*

(Continued)

*Primary Examiner*—Marc S. Hoff
*Assistant Examiner*—Elias Desta
(74) *Attorney, Agent, or Firm*—Freedman & Associates (57) ABSTRACT

Disclosed is method of controlling an asymmetric waveform generator including the steps of providing a reference timer signal, and generating an asymmetric waveform as a combination of a first sinusoidal wave having a first frequency and a second sinusoidal wave having a second frequency approximately twice the first frequency. The generated asymmetric waveform is sampled to obtain a set of data points, which set of data points is indicative of the generated asymmetric waveform. The method includes analyzing the set of data points in terms of at least a first function relating to an ideal sinusoidal wave of the first frequency, to determine a first set of resultant values relating to the first sinusoidal wave, and analyzing the set of data points in terms of at least a second function relating to an ideal sinusoidal wave of the second frequency, to determine a second set of resultant values relating to the second sinusoidal wave. In dependence upon the first set of resultant values and the second set of resultant values, a feedback signal for controlling the asymmetric waveform generator is provided.

21 Claims, 6 Drawing Sheets

U.S. PATENT DOCUMENTS 6,556,952 B1 * 4/2003 Magro .................... 702/183

FOREIGN PATENT DOCUMENTS

| EP | 0 854 366 A1 | 7/1998 |
|---|---|---|
| WO | WO 92/15150 A1 | 9/1993 |
| WO | WO 2004/030022 A2 | 4/2004 |
| WO | WO 2004/030023 A2 | 4/2004 |

OTHER PUBLICATIONS

Coleman, 'A Propagation Model for HF Radiowave Systems', 1994, IEEE Publication, pp. 875-879.*

Hou et al., 'Incorporation of Optimal Timeouts into Distributed Real-Time Load Sharing', May 1994, IEEE Publication, vol. 43, No. 5, pp. 528-547.*

Mason et al., "Transport Properties of Ions in Gases", Wiley (1988), NY, USA.

Eiceman et al., "Ion Mobility Spectrometry", (1994), CRC Press, FL, USA.

Guevremont R. et al., "Atmospheric pressure ion focusing in a high-field asymmetric waveform ion mobility spectrometer" Review of Scientific Instruments, American Institute of Physics, New York, US, vol. 70, No. 2, Feb. 1999, pp. 1370-1383.

Purves et al., "Mass spectrometric characterization of a high-field asymmetric waveform ion mobility spectrometer", Review of Scientific Instruments, vol. 69, No. 12, pp. 4094-4105, American Institute of Physics, Dec. 1998.

* cited by examiner

AUTOMATED OPTIMIZATION OF ASYMMETRIC WAVEFORM GENERATOR LC TUNING ELECTRONICS

CROSS-REFERENCE TO RELATED APPLICATIONS

This application claims the benefit of U.S. Provisional Application No. 60/486,284, filed on Jul. 11, 2003.

FIELD OF THE INVENTION

The instant invention relates generally to high field asymmetric waveform ion mobility spectrometry (FAIMS), more particularly the instant invention relates to a method of optimizing asymmetric waveform generator LC tuning electronics.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994), which is incorporated by reference herein. In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength, and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, N.Y., 1988), which is incorporated by reference herein, teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in FAIMS on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 μs followed by −1000 V for 20 μs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform, an ion moves with a y-axis velocity component given by $v_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $v_L = K E_L$, where K is the low field ion mobility under operating pressure and temperature conditions. The distance traveled is $d_L = v_L t_L = K E_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H < K$, the ion experiences a net displacement from its original position relative to the y-axis. For example, if a positive ion travels farther during the positive portion of the waveform, for instance $d_H < d_L$, then the ion migrates away from the second electrode and eventually will be neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

In FAIMS, the optimum dispersion voltage waveform for obtaining the maximum possible ion detection sensitivity on a per cycle basis takes the shape of an asymmetric square wave with a zero time-averaged value. In practice this asymmetric square waveform is difficult to produce and apply to the FAIMS electrodes because of electrical power consumption considerations. For example, without a tuned circuit the power that is required to drive a capacitive load of capacitance C, at frequency f, with a peak voltage V and a 1:1 duty cycle square wave, is $V^2fC$. Accordingly, if a square wave at 750 kHz, 4000 V peak voltage 1:1 duty cycle is applied to a 20 picofarad load, the theoretical power consumption will be 480 Watts produced by the sum of the squares of the voltage changes on the capacitive load of $4000^2+4000^2$ multiplied by f*C. If, on the other hand, a waveform is applied via a tuned circuit with Q factor (Bandwidth 3 dB/Frequency) of 200, the power consumption is reduced to less than 2.5 Watts. Theoretically the power is $P(\cos(\Phi))$ where $\Phi$ is the angle between the current and the voltage applied to the capacitive load, and P is $2V^2fC$. This power consumption approaches zero if the current and voltage are out of phase by 90 degrees, as they would be in a perfectly tuned LC circuit with ideal components. Similarly, if the waveform is asymmetrical with duty cycle of 2:1, as for example in a FAIMS application, then the theoretical power consumption is reduced to 333 Watts, produced by the sum of squares of the voltage changes on the capacitive load of $4000^2+2000^2+(2000^2-1333^2)$ times f*C.

Since a tuned circuit cannot provide a square wave, an approximation of a square wave is taken as the first terms of a Fourier series expansion. One approach is to use:

$$V(t) = \frac{2}{3}D\sin(\omega t) + \frac{1}{3}D\sin(2\omega t - \pi/2) \quad (1)$$

Where V(t) is the asymmetric waveform voltage as a function of time, D is the peak voltage (defined as dispersion voltage DV), $\omega$ is the waveform frequency in radians/sec. The first term is a sinusoidal wave at frequency $\omega$, and the second term is a sinusoidal wave at double the frequency of the first sinusoidal wave, $2\omega$. The second term is optionally represented as a cosine, without the phase shift of $\pi/2$.

In practice, both the optimization of the LC tuning and maintenance of the exact amplitude of the first and second applied sinusoidal waves and the phase angle between the two waves is required to achieve long term, stable operation of a FAIMS system powered by such an asymmetric waveform generator. Accordingly, feedback control is required to ensure that the output signal is stable and that the correct waveform shape is maintained.

In U.S. Pat. No. 5,801,379, issued on Sep. 1, 1998, which is incorporated by reference herein, Kouznetsov teaches a high voltage waveform generator having separate phase correction and amplitude correction circuits. This system uses additional components in the separate phase correction and amplitude correction circuits, thereby increasing complexity and increasing the cost of manufacturing and testing the devices. Furthermore, this system cannot be implemented in the control software, making it difficult to vary certain parameters.

It is an object of the instant invention to provide a method of optimizing asymmetric waveform generator LC tuning electronics that overcomes the limitations of the prior art.

SUMMARY OF THE INVENTION

In accordance with an aspect of the instant invention, there is provided a method of controlling an asymmetric waveform generator, comprising: using a reference timer, providing a reference timer signal; using an asymmetric waveform generator, generating an asymmetric waveform as a combination of a first sinusoidal wave having a first frequency and a second sinusoidal wave having a second frequency approximately twice the first frequency; sampling the generated asymmetric waveform to obtain a set of data points that is indicative of the generated asymmetric waveform, a rate of the sampling being determined in dependence upon the reference timer signal, and each data point of the set of data points having a known relationship relative to the reference timer signal; analyzing the set of data points in terms of at least a first function relating to an ideal sinusoidal wave of the first frequency, to determine a first set of resultant values relating to the first sinusoidal wave; analyzing the set of data points in terms of at least a second function relating to an ideal sinusoidal wave of the second frequency, to determine a second set of resultant values relating to the second sinusoidal wave; and, in dependence upon the first set of resultant values and the second set of resultant values, providing a feedback signal for controlling the asymmetric waveform generator.

In accordance with another aspect of the instant invention, there is provided an apparatus for controlling an asymmetric waveform generator, the asymmetric waveform generator for generating an asymmetric waveform as a combination of a first sinusoidal wave having a first frequency and a second sinusoidal wave having a second frequency approximately twice the first frequency, the apparatus comprising: a sampler, connectable to the asymmetric waveform generator, for sampling an output waveform from the asymmetric waveform generator and for providing data relating to a digital representation of the output waveform; a processor in communication with the sampler for receiving the data therefrom, the processor for determining a first set of resultant values based on the data by the application of at least a first function relating to an ideal sinusoidal wave of the first frequency, for determining a second set of resultant values based on the data by the application of at least a second function relating to an ideal sinusoidal wave of the second frequency, and for determining a feedback signal in dependence upon the first set of resultant values and the second set of resultant values; and, a feedback circuit in communication with the processor and with the asymmetric waveform generator, for receiving the feedback signal from the processor and for providing the feedback signal to the asymmetric waveform generator.

In accordance with yet another aspect of the instant invention, there is provided a storage medium encoded with machine-readable computer program code for controlling an asymmetric waveform generator, the asymmetric waveform generator for generating an asymmetric waveform as a combination of a first sinusoidal wave having a first frequency and a second sinusoidal wave having a second frequency approximately twice the first frequency, the storage medium including instructions for: sampling the generated asymmetric waveform to obtain a set of data points indicative of the generated asymmetric waveform, a rate of the sampling being determined in dependence upon a reference timer signal; applying to the set of data points at least a first function relating to an ideal sinusoidal wave of the first frequency, to determine a first set of resultant values; applying to the set of data points at least a second function relating to an ideal sinusoidal wave of the second frequency, to determine a second set of resultant values; and, in dependence upon the first set of resultant values and the second set of resultant values, determining a feedback signal for controlling the asymmetric waveform generator.

U.S. Provisional Patent Application No. 60/486,284, filed on Jul. 11, 2003, is incorporated by reference herein.

BRIEF DESCRIPTION OF THE DRAWINGS

Exemplary embodiments of the invention will now be described in conjunction with the following drawings, in which similar reference numerals designate similar items.

DESCRIPTION OF THE PREFERRED EMBODIMENTS

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1A:
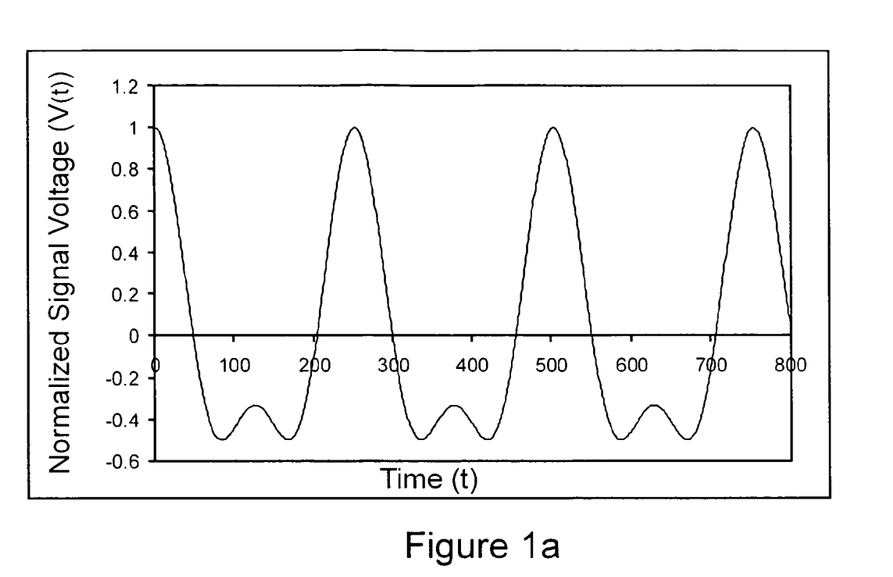
FIG. 1a shows an ideal output waveform produced by the application of two sinusoidal waves of frequency ω and 2ω.
Figure 1B:
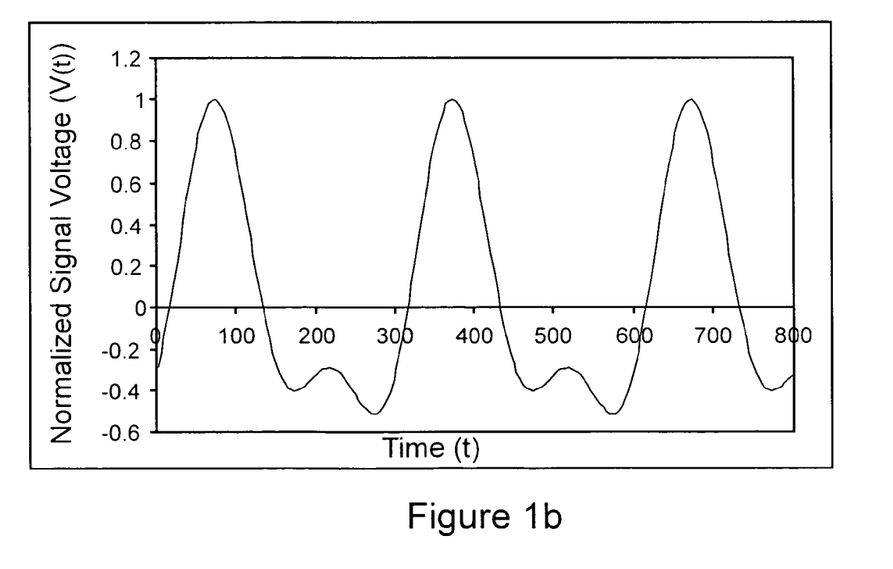
FIG. 1b shows an output waveform produced by the application of two sinusoidal waves of frequency ω and 2ω, with a small error in phase angle Θ between two sinusoidal waves of frequency ω and 2ω.
Figure 1C:
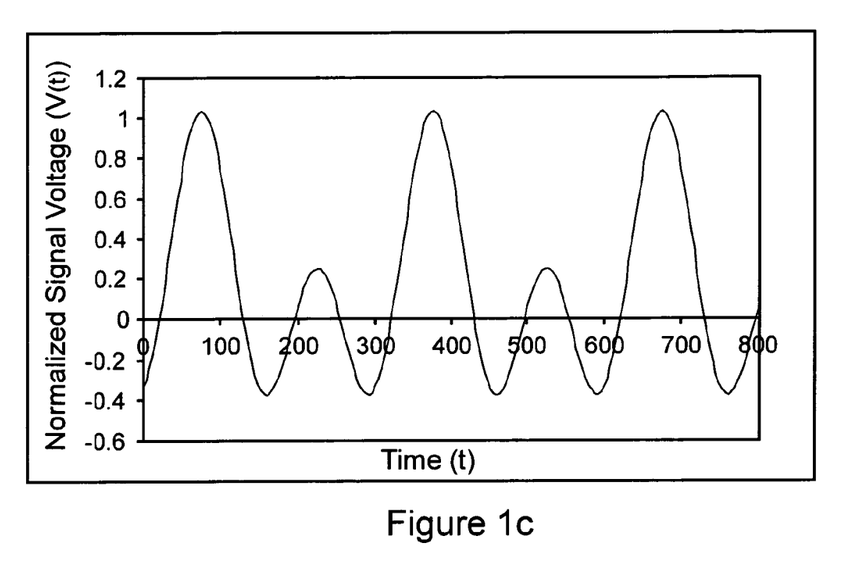
FIG. 1c shows an output waveform produced by the application of two sinusoidal waves of frequency ω and 2ω, with a large error in relative amplitudes of two sinusoidal waves of frequency ω and 2ω.

As is noted above, the waveform that is applied in FAIMS is a combination of two sinusoidal waves of frequency ω and 2ω. The two sinusoidal waves are of amplitudes that differ by a factor of two and are also offset by a phase angle (Θ), resulting in a waveform that is defined by, for example, Equation 2, below:

$$V(t) = A \sin(\omega t) + B \sin(2\omega t - \Theta) \quad (2)$$

where V(t) is the asymmetric waveform voltage as a function of time, A is the amplitude of the first sinusoidal wave at frequency ω, where ω is the waveform frequency in radians/sec, and B is the amplitude of the second sinusoidal wave at a frequency 2ω. The second sinusoidal wave is offset from the first by a phase angle Θ, which preferably is equal to π/2. In a waveform having an ideal shape, A=2B, Θ is equal to π/2, and the peak voltage on the higher voltage side of the asymmetric waveform (defined above as the dispersion voltage, DV) is constant, and equal to A+B. FIG. 1a shows an ideal output waveform produced by the application of two sinusoidal waves of frequency ω and 2ω. FIG. 1b shows an output waveform with a small error in phase angle Θ between the two sinusoidal waves of frequency ω and 2ω. FIG. 1c shows an output waveform with a large error in relative amplitudes of the two sinusoidal waves of frequency ω and 2ω.

Figure 2:
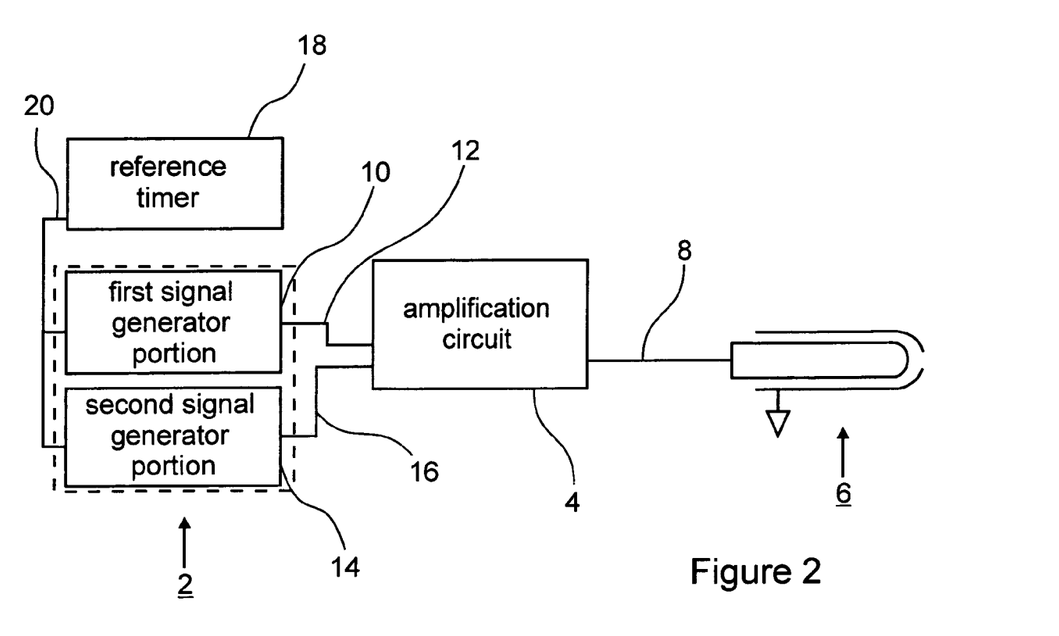
FIG. 2 shows a simplified block diagram of a system for generating an asymmetric waveform, including a set of FAIMS electrodes that are powered by said system.
Figure 3:
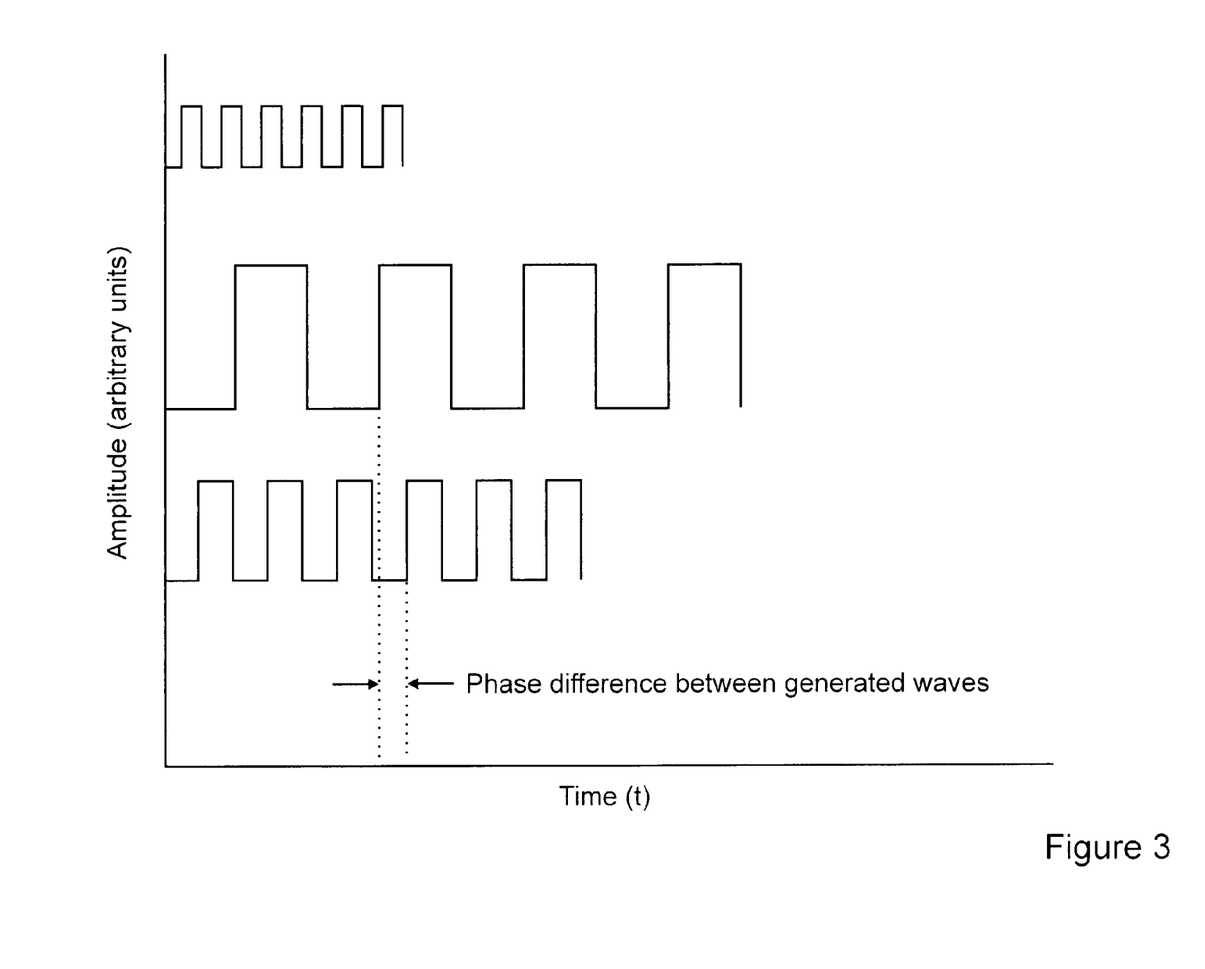
FIG. 3 shows a representation of: a reference signal provided by a reference timer of the system of FIG. 2 (upper trace); a low voltage, accurate square wave precursor of the sinusoidal wave of frequency ω (middle trace); and, a low voltage, accurate square wave precursor of the sinusoidal wave of frequency 2ω (lower trace)

Referring now to FIG. 2, shown is a simplified block diagram of a system for generating an asymmetric waveform. The FAIMS electrodes that are powered by this system are also shown at FIG. 2. The system comprises a signal generator shown generally at 2 and an amplification circuit 4, which communicate with the FAIMS electrodes 6 via a conductive port 8. The signal generator 2 produces two electrical output signals including a low voltage, accurate square wave precursor of the lower frequency sinusoidal wave (middle trace of FIG. 3), and a low voltage, accurate square wave precursor of the higher frequency sinusoidal wave (lower trace of FIG. 3). Using a reference signal (upper trace of FIG. 3) that is provided from a reference timer 18 via conductive port 20, the signal generator 2 produces the two sinusoidal waves with an accurate, digitally controlled, phase difference. For instance, signal generator 2 includes a first signal generator portion 10 for providing a lower frequency electrical output signal to amplification circuit 4 via conductive port 12, and a second signal generator portion 14 for providing a higher frequency electrical output signal to amplification circuit 4 via conductive port 16. In the amplification circuit 4, the two electrical output signals of the signal generator 2 are amplified to provide the power to drive two not illustrated tuned oscillator circuits. The power provided to each oscillator circuit is adjustable digitally, so as to control the voltage amplitude of an output sinusoidal wave of each oscillator circuit. The output sinusoidal waves of each oscillator circuit are electrically summed, and applied as the high voltage asymmetric waveform to the FAIMS electrodes 6, via the conductive port 8. Throughout this document the system shown generally at FIG. 2, excluding the FAIMS electrodes 6, will be referred to as an asymmetric waveform generator.

Several adjustments and optimizations may occur in order for the asymmetric waveform generator to automatically produce an asymmetric waveform of a desired dispersion voltage. First, the two oscillator circuits that are used to produce the output sinusoidal waves are tuned by adjustment of a not illustrated variable capacitance. By ensuring that the two oscillator circuits are "in tune", the voltage of each output sinusoidal wave is maximized and the power consumption is minimized (and the so-called 'quality' factor of each oscillator circuit is maximized). Secondly, the amplitude of each of the two output sinusoidal waves is adjusted, and a phase angle between the two output sinusoidal waves is modified, so that the expected relative amplitude and phase angle relationships between the two output sinusoidal waves are reached. The process of tuning the oscillators and adjusting amplitudes and phase angles is carried out preferably under microprocessor control.

Of course, effects of temperature, gas composition or flows in FAIMS, position of the FAIMS electrodes, position of cables, and other factors may change the capacitance of the FAIMS electrodes 6. Since the FAIMS electrodes 6 are the 'load' that is driven by the asymmetric waveform generator, these electrodes are a part (capacitive) of the oscillator circuits. Changes in impedance, particularly the capacitance of the FAIMS electrodes 6, will de-tune the oscillator circuits. In practice, both the tuning of the two oscillator circuits and maintenance of the exact relative amplitudes of the two output sinusoidal waves and the phase angle between the two output sinusoidal waves is required to achieve long term, stable operation of a FAIMS system powered by such an asymmetric waveform generator. Accordingly, feedback control is required to ensure that the output signal is stable and that the correct waveform shape shown at FIG. 1a is maintained.

Figure 4:
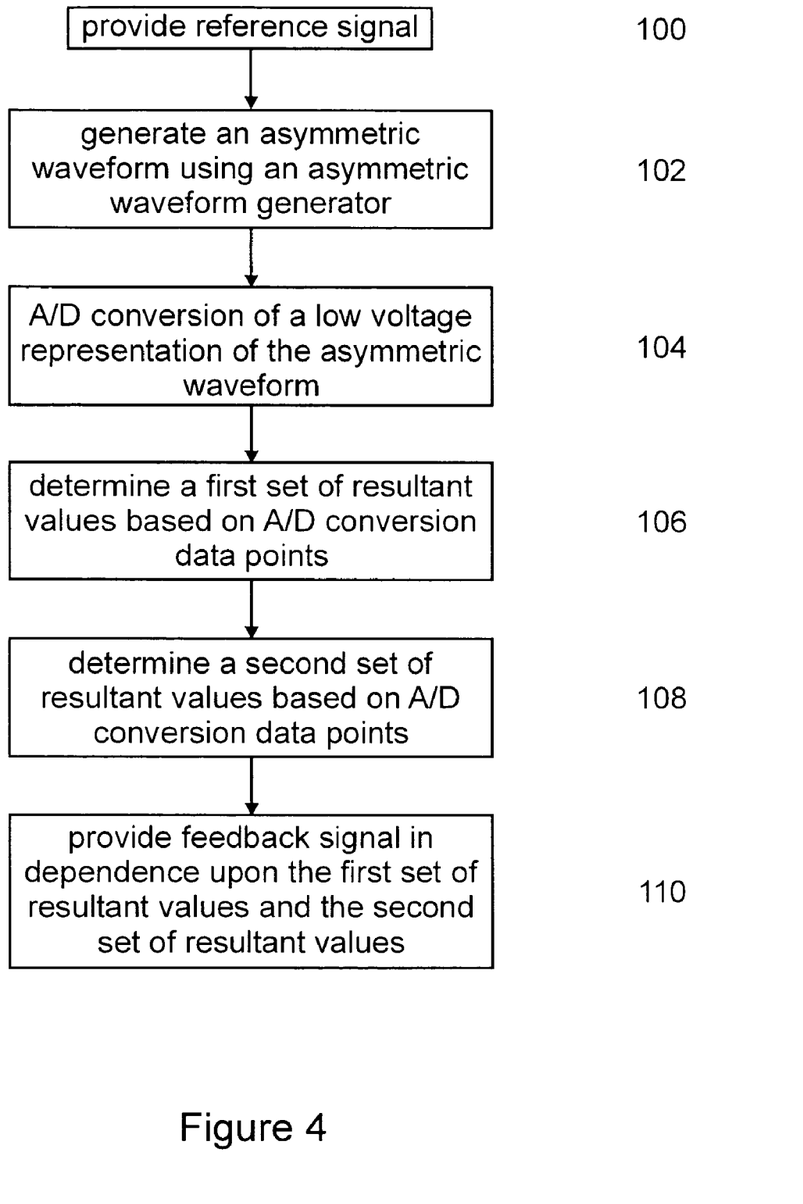
FIG. 4 is a simplified flow diagram for a method of controlling an asymmetric waveform generator according to an embodiment of the instant invention.

Referring now to FIG. 4, shown is a simplified flow diagram for a method of optimizing asymmetric waveform generator LC tuning electronics according to an embodiment of the instant invention. At step 100, a reference timer signal is provided. For instance, a reference timer is used to provide the reference timer signal. At step 102, an asymmetric waveform generator is used to generate an asymmetric waveform as a combination of a first sinusoidal wave having a first frequency and a second sinusoidal wave having a second frequency approximately twice the first frequency. At step 104, an analog-to-digital (A/D) conversion of a low voltage representation of the asymmetric waveform is performed. For instance, the generated asymmetric waveform is sampled to obtain a set of data points that is indicative of the generated asymmetric waveform, a rate of the sampling being determined in dependence upon the reference timer signal, and each data point of the set of data points having a known relationship relative to the reference timer signal. At step 106, a first set of resultant values is determined based on the A/D conversion data points. For instance, the set of data points is analyzed in terms of at least a first function relating to an ideal sinusoidal wave of the first frequency, to determine the first set of resultant values. At step 108, the set of data points is analyzed in terms of at least a second function relating to an ideal sinusoidal wave of the second frequency, to determine the second set of resultant values. At step 110, in dependence upon the first set of resultant values and the second set of resultant values, a feedback signal is provided for controlling the asymmetric waveform generator.

Figure 5:
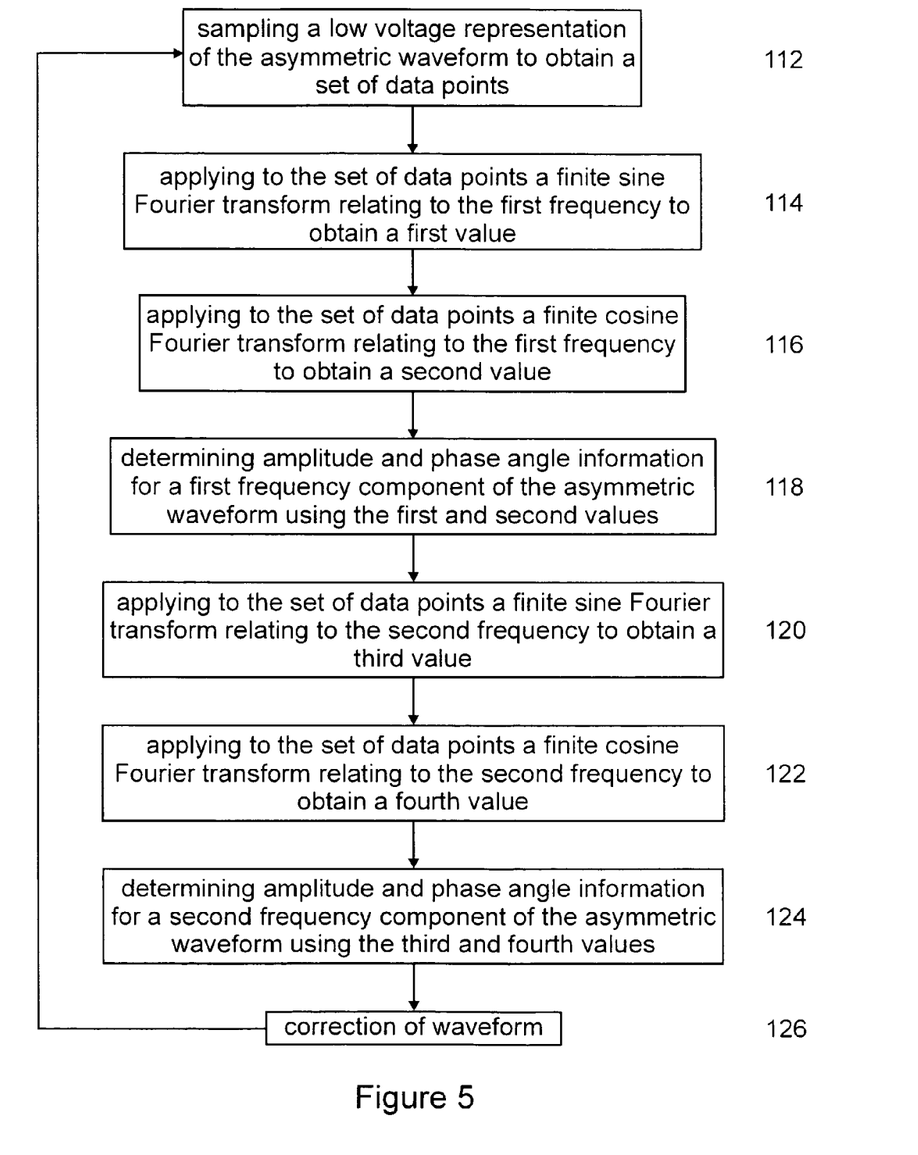
FIG. 5 is a simplified flow diagram for a method of controlling an asymmetric waveform generator according to another embodiment of the instant invention; and, FIG. 6 is a simplified block diagram of a system for generating an asymmetric waveform with feedback control according to an embodiment of the instant invention, including a set of FAIMS electrodes that are powered by said system.

Referring now to FIG. 5, shown is a simplified flow diagram for a method of optimizing asymmetric waveform generator LC tuning electronics according to another embodiment of the instant invention. At step 112 a low voltage representation of the asymmetric waveform is sampled by an analog-to-digital (A/D) conversion circuit. Since the voltage of the asymmetric waveform that is delivered to the FAIMS electrode is very high, and the circuit is a delicately balanced LC oscillator, provision is made to ensure that this measurement is representative of the actual asymmetric waveform, and that the measurement does not itself distort the output waveform.

The asymmetric waveform that is delivered to the FAIMS electrodes 6 may be phase shifted relative to the original precursor square waves that are produced by the signal generator 2. Accordingly, the reference signal shown at FIG. 3 (upper trace), which is used to produce the two precursor waves, is also used to establish the timing of the A/D conversion. The A/D conversion is started at a reference point in time, which is defined relative to the reference signal, and a set of data points is collected for a period of time exactly equal to one period of the asymmetric waveform. For ease of discussion, it is assumed that n data points are acquired for one cycle of the asymmetric waveform. For example, if 100 data points are acquired, then n=100. The variable 'x' is used to denote one of these data points, where x=1 is the first acquired data point, and x=100 is the final data point to be acquired in this example. With this accurate control of reference time, each series of A/D conversions is always taken relative to a fixed point on the low frequency precursor square wave from the signal generator. The n data points of the A/D conversion for one complete oscillation of the waveform are collected and stored in digital memory. Since the waveform is produced from a digitally controlled signal generator 2, the start point and end point of one complete cycle of the waveform is very well established with reference to the reference signal.

At step 114, a finite sine Fourier transform relating to an ideal sinusoidal wave of the first frequency is applied to the set of data points, to determine a first value, $Q_1$. For instance, each data point of the digitally stored A/D representation of the asymmetric waveform is multiplied by the value of a 'reference' sinusoidal waveform of the first frequency with unity amplitude and no phase offset relative to the reference timer signal. If n=100 A/D data points are acquired, each data point is multiplied by $\sin[x(2\pi/100)]$ where x is the number of the data point. The 100 values thus computed are added together to yield a value $q_1$. The first value, $Q_1$, is computed from $q_1$, by division of $q_1$, by n/2. In other words $Q_1=2q_1/n$. This adjustment accounts for the fact that the product of the multiplication above should be integrated from zero to $2\pi$ radians, rather than the data points being merely added together, which is more convenient and faster than integration using a microprocessor.

Similarly, at step 116 a finite cosine Fourier transform relating to an ideal sinusoidal wave of the first frequency is applied to the set of data points, to determine a second value, $R_1$. For instance, each data point of the stored A/D representation of the asymmetric waveform is multiplied by $\cos(x(2\pi/100))$, where x represents the number of the corresponding A/D data point. The 100 values thus computed are added together to yield a value $r_1$. As above, the second value $R_1$ is computed from $r_1$, by division of $r_1$, by n/2. In other words $R_1=2r_1/n$.

It should be noted that performing steps 114 and 116 in combination, as described supra, is equivalent to analyzing the set of data points in terms of at least a first function relating to an ideal sinusoidal wave of the first frequency, to determine a first set of resultant values relating to the ideal sinusoidal wave of the first frequency. In this case, the first set of resultant values consists of $Q_1$ and $R_1$.

At step 118, the value of the amplitude of the first frequency component of the waveform is calculated from the first and second values $Q_1$ and $R_1$, respectively. In this case the amplitude is the square root of the sum of squares of $Q_1$ and $R_1$, i.e. ampltiude=sqrt($Q_1^2+R_1^2$).

It is important to note that in this particular case, the Fourier transform has been done in such a way that $Q_1$ and $R_1$ do not reflect any aspect of the amplitude or phase angle of the higher frequency harmonic, because this harmonic is exactly twice the frequency of the lower frequency. The method described with reference to FIG. 5 very specific to the case of the asymmetric waveform that is composed of a first frequency component and a second frequency component that is exactly twice the frequency of the first.

The values of $Q_1$ and $R_1$ also yield the value of the phase angle between the sinusoidal wave of low frequency in the asymmetric waveform and the artificially created sine (or cosine) waves used at steps 114 and 116. For example, the phase difference may be calculated from the arctangent of the ratio of $Q_1$ to $R_1$. Of course, an additional step must be taken to obtain a value of the correct sign, plus or minus. For instance, this step includes calculation of the arcsine and the arccosine of $Q_1$ and $R_1$.

Optionally, at least some of the above-mentioned calculations involving trigonometric functions use values of these functions that are tabulated in digital memory of a microprocessor. In practice the number of A/D steps are predefined and remain constant, therefore any other functions, including arctangent need only be tabulated for this same number of steps.

Since the asymmetric waveform used in FAIMS is composed of a lower frequency and a second higher frequency sinusoidal wave at twice the frequency of the lower, it is also necessary to use the above Fourier transform method to obtain the amplitude and phase shift of this second sinusoidal wave.

Accordingly, steps 120 to 124 are performed in a manner similar to that described with reference to steps 114 to 118, except the finite sine Fourier transform and the finite cosine Fourier transform relate to an ideal sinusoidal wave of the second frequency. For instance, instead of multiplying the A/D version of the waveform by a sinusoidal wave of the lower frequency, this multiplication uses a sinusoidal wave of the higher frequency. Similarly, the A/D version of the waveform is multiplied by a cosine wave of the higher frequency. All the steps that follow these multiplication steps are identical to those noted above, including addition of all the computed values, calculation of a third value $Q_2$ and a fourth value $R_2$ and the use of $Q_2$ and $R_2$ to determine the amplitude and phase angle. Of course, the amplitude thus computed corresponds to the amplitude of the higher frequency component of the asymmetric waveform and the phase angle corresponds to the angle between the reference sinusoidal wave and the corresponding higher frequency component sine wave of the asymmetric waveform.

It should be noted that performing steps 120 and 122 in combination, as described supra, is equivalent to analyzing the set of data points in terms of at least a second function relating to an ideal sinusoidal wave of the second frequency, to determine a second set of resultant values relating to the ideal sinusoidal wave of the second frequency. In this case, the second set of resultant values consists of $Q_2$ and $R_2$.

Four important values have been computed from the values $Q_1$, $R_1$, $Q_2$ and $R_2$. In particular, the four important values are the amplitudes of the lower and higher frequency sinusoidal waves of which the asymmetric waveform is composed, as well as two phase angles. Subtraction of these two phase angles provides the phase angle between the lower and higher frequency component of the asymmetric waveform.

The correction of the waveform at step 126, if any adjustment is necessary, is based upon the four important values calculated above. For example, if the amplitude of one of the waves is below the required value, a feedback signal is provided to the amplifier circuit of the corresponding frequency wave (i.e. to one of the first signal generator portion 10 and the second signal generator portion 14), and the amplitude is modified accordingly. If the computed phase angle difference differs from the required value, this angle is adjusted by sending a signal to the signal generator 2 so that the digitally controlled difference in the phase angles is modified to correspond to the expected value.

Although the steps described appear to control the relative amplitudes of both the low and high frequency components of the waveform, plus their relative phase angle difference, the control of the waveform generator also requires that the tuning of the LC oscillators of both frequencies be monitored and adjusted to maintain optimum voltage output with minimum power requirements (highest possible values of 'quality' of each oscillator).

The tuning of the high and low frequency components of the waveform requires adjustment of a not illustrated variable capacitor in order to compensate for temperature changes, and other environmental factors that change the load capacitance of the LC circuit. Based upon the calculations described above with reference to FIG. 5, a phase angle of each frequency component of the asymmetric waveform relative to the corresponding wave generated by the signal generator 2 is determined. From a theoretical point of view, the oscillator is tuned when the phase difference between the drive frequency (from the signal generator 2) and the output frequency (from the amplification circuit 4) is reduced to zero. Because in practice the output of the signal generator 2 is amplified prior to application to the LC tank circuit, an inherent phase shift has taken place during this amplification. The value of this phase shift is determined empirically, and the expected phase shift for optimum tuning is thus established. If during operation the computed phase angle drifts from this expected value, the variable capacitor is adjusted until the computed phase angle corresponds to the expected value for improved tuning.

Figure 6:
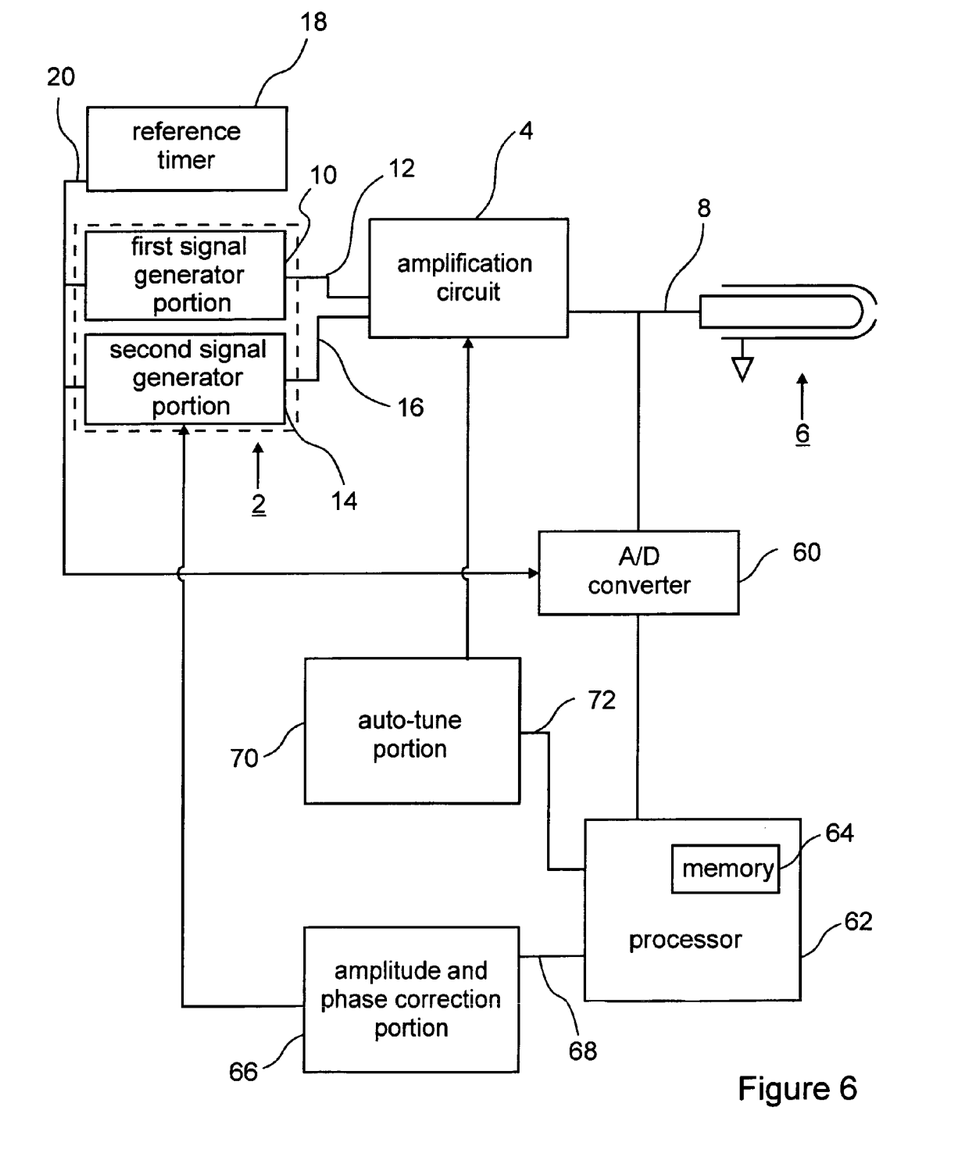

Referring now to FIG. 6, shown is a simplified block diagram of a system for generating an asymmetric waveform with feedback control according to an embodiment of the instant invention. The FAIMS electrodes that are powered by this system are also shown at FIG. 6. The system comprises a signal generator shown generally at 2 and an amplification circuit 4, which communicate with the FAIMS electrodes 6 via a conductive port 8. The signal generator 2 produces two electrical output signals including a low voltage, accurate square wave precursor of the lower frequency sinusoidal wave (middle trace of FIG. 3), and a low voltage, accurate square wave precursor of the higher frequency sinusoidal wave (lower trace of FIG. 3). Using a reference signal (upper trace of FIG. 3) that is provided from a reference timer 18 via conductive port 20, the signal generator 2 produces the two sinusoidal waves with an accurate, digitally controlled, phase difference. For instance, signal generator 2 includes a first signal generator portion 10 for providing a lower frequency electrical output signal to amplification circuit 4 via conductive port 12, and a second signal generator portion 14 for providing a higher frequency electrical output signal to amplification circuit 4 via conductive port 16. In the amplification circuit 4, the two electrical output signals of the signal generator 2 are amplified to provide the power to drive two not illustrated tuned oscillator circuits. The power provided to each oscillator circuit is adjustable digitally, so as to control the voltage amplitude of an output sinusoidal wave of each oscillator circuit. The output sinusoidal waves of each oscillator circuit are electrically summed, and applied as the high voltage asymmetric waveform to the FAIMS electrodes 6, via the conductive port 8. Collectively, the signal generator 2 and the amplifier circuit comprise an asymmetric waveform generator.

Referring still to FIG. 6, an analog-to-digital (A/D) converter 60 is provided in communication with the waveform generator. The A/D converter 60 samples a low voltage representation of the asymmetric waveform. Since the voltage of the asymmetric waveform that is delivered to the FAIMS electrode 6 is very high, and the circuit is a delicately balanced LC oscillator, provision is made to ensure that this measurement is representative of the actual asymmetric waveform, and that the measurement does not itself distort the output waveform. The A/D converter 60 is in communication with a processor 62 having a memory 64. Data points that are sampled by the A/D converter 60 are provided to the processor 62 and stored in memory 64. The processor is for determining at least a feedback signal according to a method described supra. The at least a feedback signal is provided to at least one of an amplitude and phase correction portion 66 of a feedback circuit via conductive port 68, and an auto-tune portion 70 of the feedback circuit via conductive port 72. The amplitude and phase correction portion 66 adjusts at least one of the first signal generator portion 10 and the second signal generator portion 14. The auto-tune portion 70 adjusts a not illustrated variable capacitor of the amplification circuit 4.

The apparatus and method described herein provide a practical and low cost approach to establish and maintain the output of an asymmetric waveform generator used in a FAIMS system. Several pieces of information are derived from a Fourier transform applied to the data from an A/D data acquisition. The collection and timing of the A/D data acquisition are very specifically tailored to the waveform used in this application. Furthermore, a specific version of the finite sine and finite cosine Fourier transform is applicable to this problem, to extract phase angles and amplitudes of the two component waves that are used to synthesize the asymmetric waveform. The approach described herein minimizes electronic circuitry, and ensures that one set of measurements of the output waveform, taken in a very specific manner yields sufficient data to provide feedback information with which to control automatic tuning of the LC tank circuit, and to control the phases and amplitudes of the component waves that are used to synthesize the asymmetric waveform.

Numerous other embodiments may be envisaged without departing from the spirit and scope of the invention.

What is claimed is:

1. A method of controlling an asymmetric waveform generator, comprising:
   using a reference timer, providing a reference timer signal;
   using an asymmetric waveform generator, generating an asymmetric waveform as a combination of a first sinusoidal wave having a first frequency and a second sinusoidal wave having a second frequency approximately twice the first frequency;
   sampling the generated asymmetric waveform to obtain a set of data points that is indicative of the generated asymmetric waveform, a rate of the sampling being determined in dependence upon the reference timer signal, and each data point of the set of data points having a known relationship relative to the reference timer signal;
   analyzing the set of data points in terms of at least a first function relating to an ideal sinusoidal wave of the first frequency, to determine a first set of resultant values relating to the first sinusoidal wave;
   analyzing the set of data points in terms of at least a second function relating to an ideal sinusoidal wave of the second frequency, to determine a second set of resultant values relating to the second sinusoidal wave; and,
   in dependence upon the first set of resultant values and the second set of resultant values, providing a feedback signal for controlling the asymmetric waveform generator.

2. A method according to claim 1, wherein analyzing the set of data points in terms of at least a first function relating to an ideal sinusoidal wave of the first frequency comprises applying to the set of data points a finite sine Fourier transform relating to the first frequency and applying separately to the set of data points a finite cosine Fourier transform relating to the first frequency.

3. A method according to claim 2, wherein a first resultant value of the first set of resultant values is based on a result of the finite sine Fourier transform relating to the first frequency, and a second resultant value of the first set of resultant values is based on a result of the finite cosine Fourier transform relating to the first frequency.

4. A method according to claim 2, wherein analyzing the set of data points in terms of at least a second function relating to an ideal sinusoidal wave of the second frequency comprises applying to the set of data points a finite sine Fourier transform relating to the second frequency and applying separately to the set of data points a finite cosine Fourier transform relating to the second frequency.

5. A method according to claim 4, wherein a first resultant value of the second set of resultant values is based on a result of the finite sine Fourier transform relating to the second frequency, and a second resultant value of the second set of resultant values is based on a result of the finite cosine Fourier transform relating to the second frequency.

6. A method according to claim 4, wherein information relating to at least one of an amplitude and a phase angle of the first sinusoidal wave is determined based on the first set of resultant values.

7. A method according to claim 6, wherein information relating to at least one of an amplitude and a phase angle of the second sinusoidal wave is determined based on the second set of resultant values.

8. A method according to claim 7, wherein the feedback signal includes information for adjusting at least one of a phase angle difference between the first sinusoidal wave and the second sinusoidal wave, and an amplitude of at least one of the first sinusoidal wave and the second sinusoidal wave.

9. A method according to claim 1, wherein the feedback signal includes information for adjusting at least one of a phase angle difference between the first sinusoidal wave and the second sinusoidal wave, and an amplitude of at least one of the first sinusoidal wave and the second sinusoidal wave.

10. A method according to claim 1, wherein sampling the generated asymmetric waveform is performed as an analog-to-digital sampling for collecting data points within one cycle of the generated asymmetric waveform.

11. A method according to claim 10, wherein each data point includes information relating to a value of V(t) at a time t, where V(t) is the asymmetric waveform voltage as a function of time.

12. A method according to claim 11, wherein a time dependent part of the generated asymmetric waveform has the general form $V(t)=A \sin(\omega t)+B \sin(2\omega t-\Theta)$, where V(t) is the asymmetric waveform voltage as a function of time, A is the amplitude of the first sine wave at frequency $\omega$ where $\omega$ is the frequency in radians/sec, B is the amplitude of the second sine wave at a frequency $2\omega$, and $\Theta$ is a phase angle offset between the first sinusoidal wave and the second sinusoidal wave.

13. A method according to claim 1, wherein analyzing the set of data points in terms of at least a first function relating to an ideal sinusoidal wave of the first frequency comprises applying to the set of data points a Fourier transform relating to the first frequency.

14. A method according to claim 13, wherein analyzing the set of data points in terms of at least a second function relating to an ideal sinusoidal wave of the second frequency comprises applying to the set of data points a Fourier transform relating to the second frequency.

15. A method according to claim 14, wherein the feedback signal includes information for adjusting at least one of a phase angle difference between the first sinusoidal wave and the second sinusoidal wave, and an amplitude of at least one of the first sinusoidal wave and the second sinusoidal wave.

16. A method according to claim 11, wherein analyzing the set of data points in terms of at least a first function relating to an ideal sinusoidal wave of the first frequency comprises applying to the set of data points a Fourier transform relating to the first frequency.

17. A method according to claim 16, wherein analyzing the set of data points in terms of at least a second function relating to an ideal sinusoidal wave of the second frequency comprises applying to the set of data points a Fourier transform relating to the second frequency.

18. A method according to claim 17, wherein the feedback signal is for adjusting at least one of a phase angle difference between the first sinusoidal wave and the second sinusoidal wave, and an amplitude of at least one of the first sinusoidal wave and the second sinusoidal wave.

19. A method according to claim 1, comprising, in dependence upon the provided feedback signal, adjusting at least one of a phase angle difference between the first sinusoidal wave and the second sinusoidal wave, and an amplitude of at least one of the first sinusoidal wave and the second sinusoidal wave.

20. An apparatus for controlling an asymmetric waveform generator, the asymmetric waveform generator for generating an asymmetric waveform as a combination of a first sinusoidal wave having a first frequency and a second sinusoidal wave having a second frequency approximately twice the first frequency, the apparatus comprising:
- a sampler, connectable to the asymmetric waveform generator, for sampling an output waveform from the asymmetric waveform generator and for providing data relating to a digital representation of the output waveform;
- a processor in communication with the sampler for receiving the data therefrom, the processor for determining a first set of resultant values based on the data by the application of at least a first function relating to an ideal sinusoidal wave of the first frequency, for determining a second set of resultant values based on the data by the application of at least a second function relating to an ideal sinusoidal wave of the second frequency, and for determining a feedback signal in dependence upon the first set of resultant values and the second set of resultant values; and,
- a feedback circuit in communication with the processor and with the asymmetric waveform generator, for receiving the feedback signal from the processor and for providing the feedback signal to the asymmetric waveform generator.

21. A storage medium encoded with machine-readable computer program code for controlling an asymmetric waveform generator, the asymmetric waveform generator for generating an asymmetric waveform as a combination of a first sinusoidal wave having a first frequency and a second sinusoidal wave having a second frequency approximately twice the first frequency, the storage medium including instructions for:
- sampling the generated asymmetric waveform to obtain a set of data points indicative of the generated asymmetric waveform, a rate of the sampling being determined in dependence upon a reference timer signal;
- applying to the set of data points at least a first function relating to an ideal sinusoidal wave of the first frequency, to determine a first set of resultant values;
- applying to the set of data points at least a second function relating to an ideal sinusoidal wave of the second frequency, to determine a second set of resultant values; and,
- in dependence upon the first set of resultant values and the second set of resultant values, determining a feedback signal for controlling the asymmetric waveform generator.

* * * * *